United States Patent [19] [11] 4,280,094
Karlsson [45] Jul. 21, 1981

[54] TEST PLATE METHOD AND AN ARRANGEMENT FOR TESTING THE SERVICEABILITY AND FOR SETTING AND CALIBRATING A TEST APPARATUS FOR THE NON-DESTRUCTIVE ELECTRICAL OR MAGNETIC TESTING OF METALLIC BLANKS

[75] Inventor: Per-Olle Karlsson, Oxelösund, Sweden

[73] Assignee: Svenskt Stal Aktiebolag, Stockholm, Sweden

[21] Appl. No.: 969,274

[22] Filed: Dec. 14, 1978

[30] Foreign Application Priority Data

Dec. 16, 1977 [DE] Fed. Rep. of Germany ....... 2756244

[51] Int. Cl.³ ...................... G01R 35/00; G01R 33/00
[52] U.S. Cl. ..................................... 324/202; 324/262
[58] Field of Search ............... 324/202, 226, 225, 237, 324/238, 240, 262; 73/1 R

[56] References Cited

U.S. PATENT DOCUMENTS

| 3,371,524 | 3/1968 | Wloszek | 73/1 R |
| 3,534,259 | 10/1970 | Harmon et al. | 324/202 |
| 3,609,529 | 9/1971 | Skubiek et al. | 324/202 |

Primary Examiner—Gerard R. Strecker
Assistant Examiner—Walter E. Snow
Attorney, Agent, or Firm—Craig and Antonelli

[57] ABSTRACT

A method and arrangement for testing the serviceability and for setting and calibrating a test apparatus for the non-destructive electrical and/or magnetic testing of metallic blanks, particularly steel slabs, for defects, such as surface or below-surface cracks, laps, shrinkholes, blowholes or the like, comprising inspecting means capable of detecting defects such as these and mounted for displacement relative to the surface of the blank to be tested, test plate simulating a defective metallic blank being brought up to the test apparatus in a position in which they are in substantial alignment with the surface of the blank to be tested, the inspecting means of the test apparatus being tested by the test plates for working order and calibrated.

19 Claims, 10 Drawing Figures

TEST PLATE METHOD AND AN ARRANGEMENT FOR TESTING THE SERVICEABILITY AND FOR SETTING AND CALIBRATING A TEST APPARATUS FOR THE NON-DESTRUCTIVE ELECTRICAL OR MAGNETIC TESTING OF METALLIC BLANKS

This invention relates to a method and an arrangement for testing the serviceability and for setting and calibrating a test apparatus for the non-destructive electrical, magnetic and/or magnetoinductive testing of metallic blanks, particularly steel slabs or heavy plates, for defects or faults, such as surface or below-surface cracks, laps, shrink holes, blow holes or the like, comprising at least one inspecting means or sensors capable of detecting defects such as these and mounted for displacement relative to the surface of the blank to be tested or scanned, the metallic blanks with different electrical and/or magnetic parameters being delivered to the test apparatus by transporting means, such as transporting rollers arranged at intervals from one another. Where test apparatus of the kind mentioned above are used for testing metallic blanks, it has repeatedly been found that, when one batch of blanks having a certain material composition, a certain thickness and certain electrical and/or magnetic parameters is changed for a batch of blanks having a different composition, a different thickness and different electrical and/or magnetic parameters, the test apparatus always have to be set and calibrated on the basis of the first blank of each batch by a laborious and complicated procedure. In addition, the electronic components involved can undergo ageing or similar changes. In addition, the sensors may develop faults and the moving structural components of the test apparatus can change as a result of natural wear. All this means that the test apparatus has to be periodically checked.

The object of the present invention is considerably to shorten this time-consuming setting up of the test apparatus and to propose measures which eliminate the need for setting and calibration on the basis of the blank itself, i.e. by which the very first blank is delivered to a test apparatus which has already been adapted to its material composition, to its thickness and to its electrical and/or magnetic parameters.

According to the invention, this object is achieved in that one or more test plates simulating a defective metallic blank and having the same electrical and/or magnetic parameters are arranged in a position in which they are in substantial alignment with the surface of the blank to be tested, and said sensor or at least a part of said sensors of the test apparatus are brought into contact with the surface of the test plate or plates and/or the surface of a test plate holder, which surface of the test plate holder is in alignment with the surface of the test plate or plates, and the sensor or at least a part of the sensors, when travelling over the test plate or plates, are tested for working order and calibrated.

Preferably, the test plates are arranged in such a way adjacent beside the path of travel along which the blanks move on the transporting system that the inspecting heads of the test apparatus preferably move over the test plates directly before and/or directly after their travel along the surface of the blank to be tested for detecting defects.

Alternatively, the test plate or plates can be introduced to the path of travel of the blanks in the transporting system, preferably between two transporting rollers, so that they are in substantial alignment with the surface of the blank to be tested, and are, after they have been travelled over by said sensors or inspecting heads of the test apparatus, moved away from the path of travel of the blanks, preferably downwardly and/or to the side.

The method according to the invention affords the advantage that 1. each individual sensor or inspecting head can be rapidly adjusted to any material composition without any delay in the flow of material, the inspecting heads preferably being adjusted simultaneously to the respective level of the surface of the blank to be inspected,
2. each individual inspecting head adapted to each blank is automatically checked both for wear and for other faults capable of altering signal strength during the determination of depth,
3. a guarantee is provided to the extent that, during defect detecting, the determination of depth remains constant from material to material and from inspecting head to inspecting head for the classification of the defects, the manual or automatic removal of defects from the blanks or grading of the blanks as faultless or scrap, after defect detection.

To enable the method described above to be carried out successfully in the case of a blank test apparatus comprising a system provided with transporting rollers for transporting the blanks, it is possible in accordance with the invention to arrange a magazine containing several test plates in the area of the blank test apparatus adjacent beside the system for transporting the blanks in such a way that it can be raised to and lowered from the level of the blank. In this connection, the test plates accommodated in the magazine may be arranged adjacent one another on a chain conveyor in its direction of movement, this chain conveyor bringing the test plate adapted to the parameters of the particular blank to be tested into an upper test position (cf. FIGS. 1 and 2).

In a modified embodiment of the above mentioned arrangement according to the invention, a magazine containing several test plates is fixedly mounted in the area of the blank testing apparatus adjacent beside the system for transporting the blanks and only that test plate which is adapted to the parameters of the material of the blank to be tested is designed to be raised to and lowered from the level of the blank. To this end, the test plates accommodated in the magazine are best arranged one behind the other on a chain conveyor in its direction of travel and only that test plate which is adapted to the particular blank to be tested is designed to be individually raised and lowered by means of a separate test plate holder in conjunction with hydraulic cylinder units (cf. FIGS. 3 and 4).

In another embodiment of a test plate holder and guide suitable for carrying out the method according to the invention, the test plate holder and magazine are arranged separate from one another. According to the invention, a holder for the particular test plate adapted to the parameters of the blank to be tested is arranged in the area of the blank test apparatus between two adjacent transporting rollers in such a way that it can be raised and lowered, the test plate being delivered to this holder from a laterally arranged test plate magazine (cf. FIGS. 5 to 8). The test plate holder consists of a vertically or substantially vertically arranged frame into the upper end of which the test plate is designed to be introduced and which along its sides at or substantially at the centre thereof is pivotally supported by one end of an angle lever. This angle lever is rotatably mounted at its centre and, at its other end, is connected to a hydraulic cylinder unit by means of which the frame can be raised and lowered. In order to make the upper edge of the frame which acts as a stop for the blanks to be tested resilient, a pull rod is pivotally mounted on the underneath of each of the lateral frame members and is guided for axial displacement against the force of a spring in a pivotal bearing. In another embodiment of the invention, the bearing in which the pull rod is axially guided is pivotable about two pivots arranged opposite one another at a right angle to the pull rod axis in a pedestal, a compression spring being arranged between the pull rod bearing and an adjusting nut screwed onto the free end of the pull rod. This spring may be a telescopic elastic spring.

Figure 9:
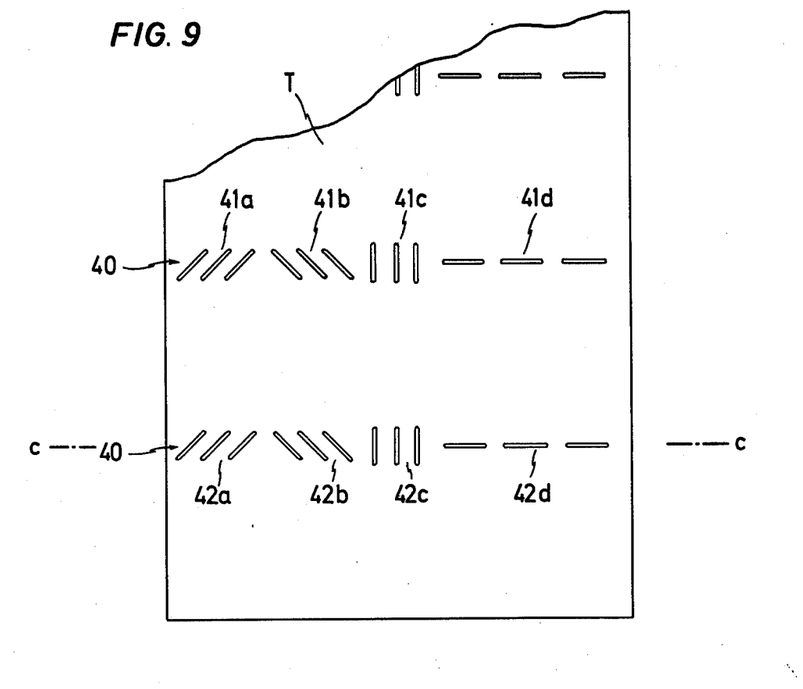
FIG. 9 is a plan view of part of the test plate.
Figure 10:
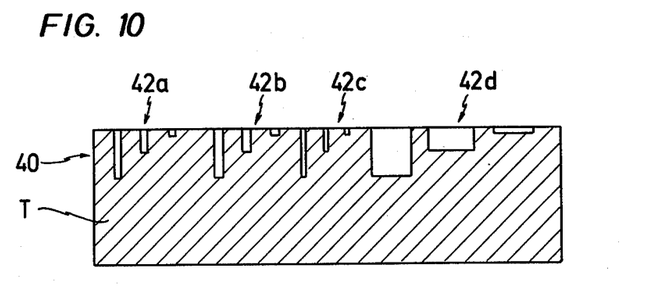
FIG. 10 is a section through the test plate shown in FIG. 9 on the line c—c.

According to the invention, the test plate used for carrying out the method is in the form of a rectangular slat and, over its length corresponding to the length or width of the blanks to be inspected, comprises several rows of narrow notches or slots which are arranged in the direction of movement of the test apparatus, and at the same intervals from one another as the sensors or inspecting heads, extend at an acute angle, at a right angle and parallel to the direction of movement of the test apparatus and differ from one another in depth (FIGS. 9 and 10). Each row best contains four groups of notches differing in their orientation, the notches arranged with the same orientation in each group having different depths which are arranged in the same way in all groups.

Three embodiments of the invention are described in the following with reference to the accompanying drawings, wherein.

Figure 1:
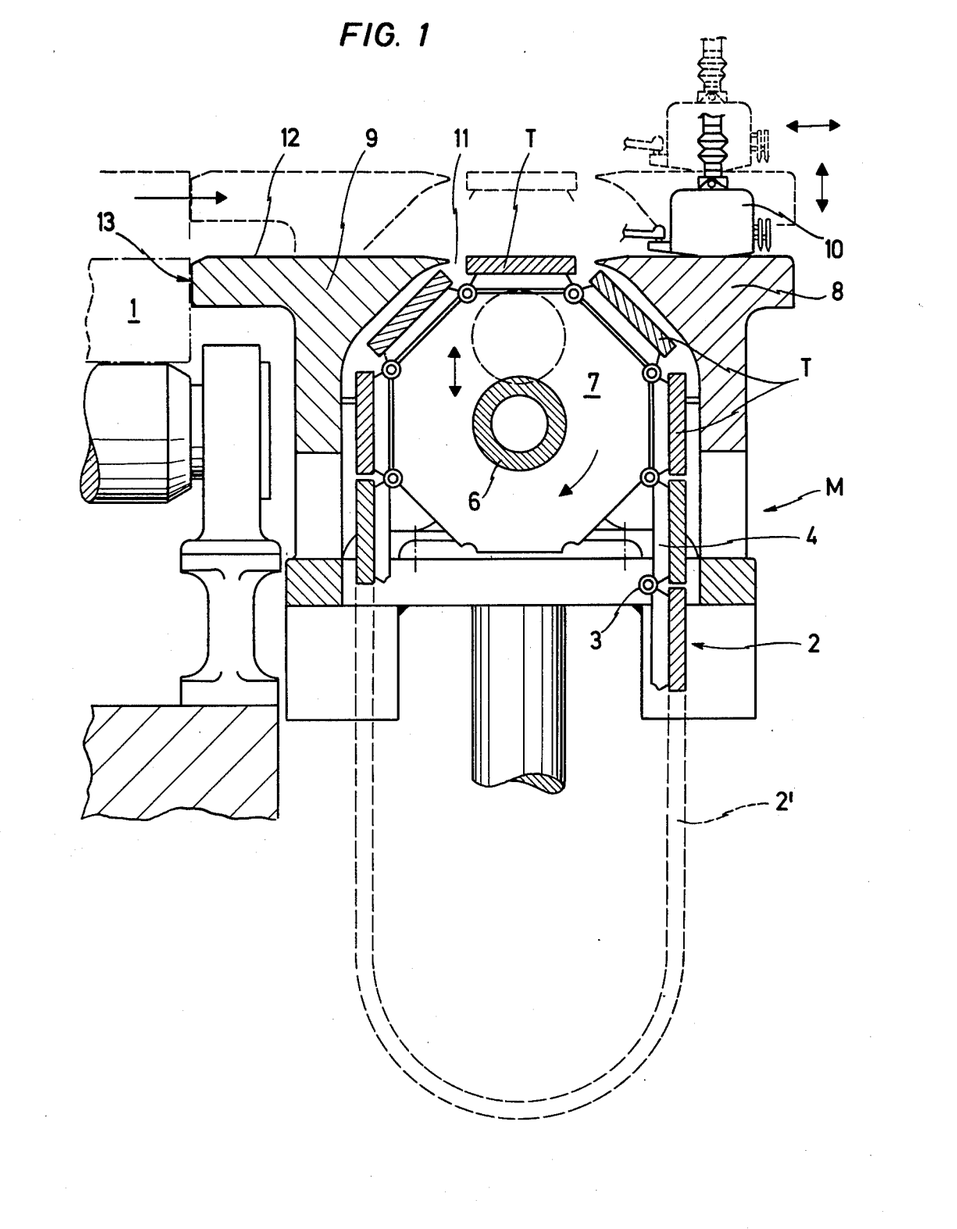
FIG. 1 is a side elevation, partly in section, of a test magazine arrangement.
Figure 2:
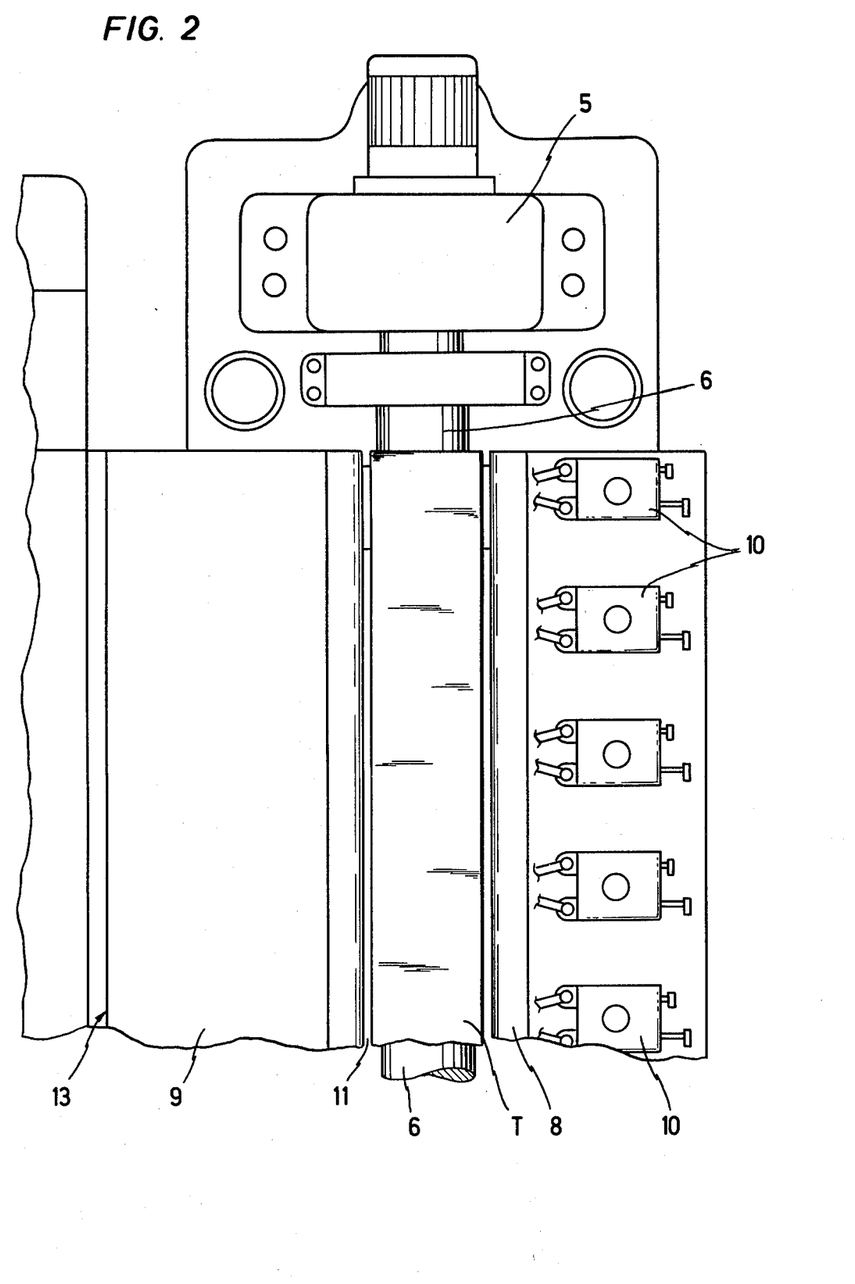
FIG. 2 is a plan view of the arrangement shown in FIG. 1.

The embodiment illustrated in FIGS. 1 and 2 of the arrangement of a magazine M containing a number of test plates T adapted to the particular blank 1 to be tested comprises a chain conveyor 2 having at least two chain conveyor belts 2' which are made up of individual links 3 and each of which is designed to be moved step-by-step by a sprocket wheel 7 driven by a geared motor 5 and mounted on a shaft 6. The test plates T are fixed to the projections 4 of the chain links 3 of these conveyor belts 2'. At its upper end, the test plate magazine M comprises right-hand and left-hand pedestals 8 and 9 for the inspecting heads 10 containing sensor means of the blank test apparatus. These pedestals are arranged in such a way that they leave a gap 11 into which the particular test plate T required can be introduced in alignment with the surface 12 of the pedestals 8 and 9.

In order to be able exactly to adapt the surface 12 of the pedestals 8 and 9 and the test plate T to the thickness of the particular metallic blank 1 to be tested, the entire test plate magazine M is designed to be raised and lowered by means (now shown), as shown in chain lines in FIG. 1. The blank 1 is transported by means of a transporting system in the direction perpendicular to the plane of the drawing, which transporting system comprises rollers, one of which is partly shown in FIG. 1. At its left-hand outside, the left-hand pedestal 9 forms a lateral stop 13 for the metallic blank 1 to be inspected after the test apparatus 10 has been tested for serviceability and calibrated. The blank 1 is moved to the right (as shown by an arrow) to abut with one of its side surfaces against the stop 13 by means of lifting cylinders (not shown) engaging the other side surface of the blank 1. After the blank 1 abuts against the stop 13, the upper surface of the test plate T and the surface 12 of the pedestals 8 and 9 are brought into alignment with the upper surface to be inspected of the individual blank 1 by raising and/or lowering the magazine M. Then the inspecting heads 10 move along the upper surface of the blank 1 transversely of the transporting direction of the transporting system, which movement of the inspecting head 10 can take place in one go with their movement over the test plate T.

Figure 3:
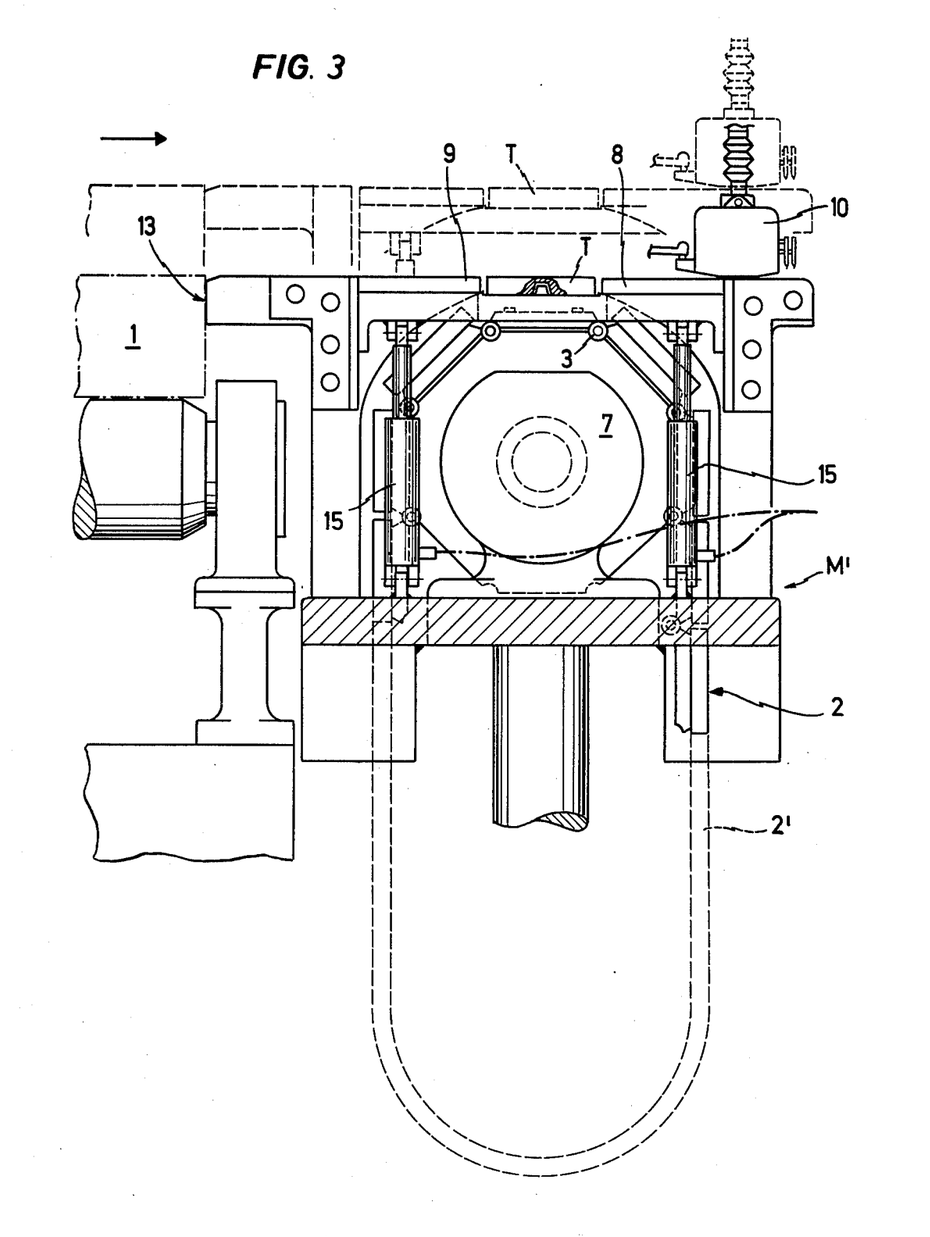
FIG. 3 is a side elevation, partly in section, of a modified embodiment of the test magazine arrangement.
Figure 4:
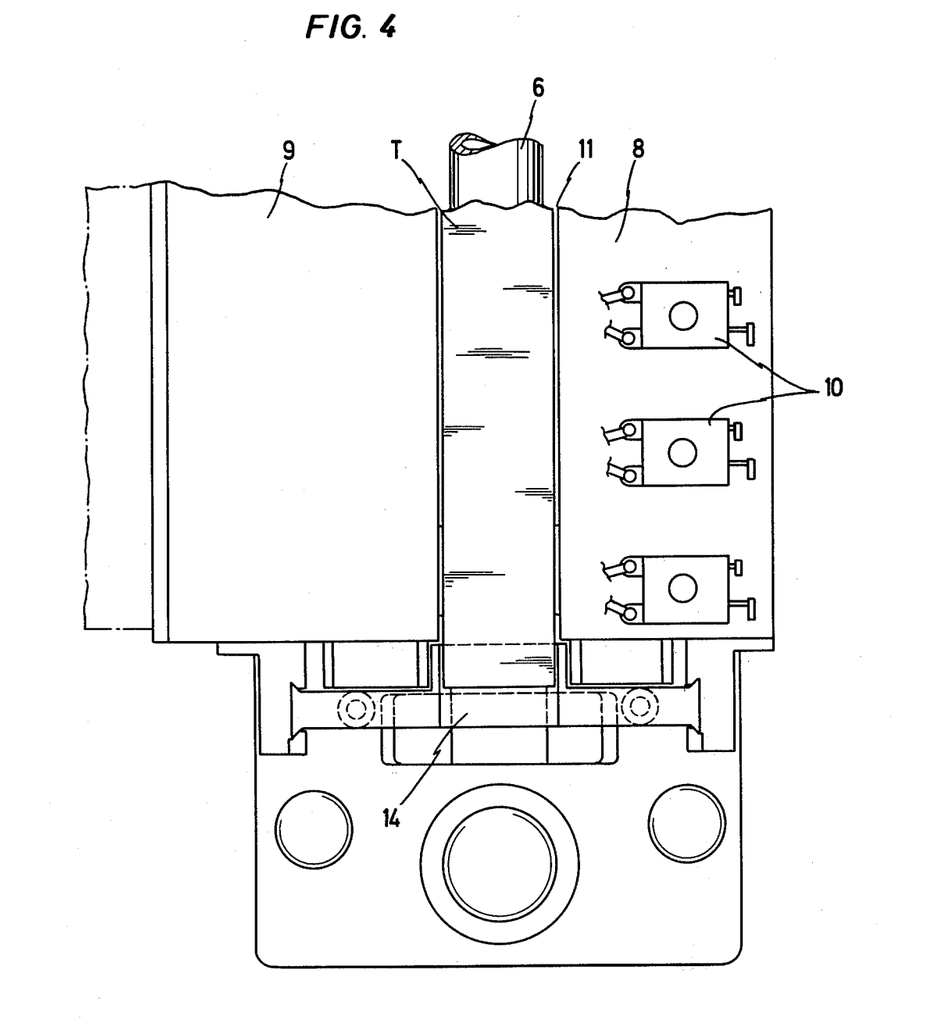
FIG. 4 is a plan view of the test magazine arrangement shown in FIG. 3.

The test plate magazine of the second embodiment illustrated in FIGS. 3 and 4 is substantially identical in its basic structure with the embodiment illustrated in FIGS. 1 and 2, except that, in this case, the test plate magazine M' is not designed to be raised and lowered in its entirety, but only the particular test plate T and its holder to be raised to the level of the blank. To this end, the right-hand and left-hand pedestals 8 and 9 for the inspecting head or heads 10 also acts as a holder for the test plate T. Only the pedestals 14 and, with them, the test plate T are designed to be raised and lowered to the required level by means of several hydraulic cylinder units 15.

Figure 5:
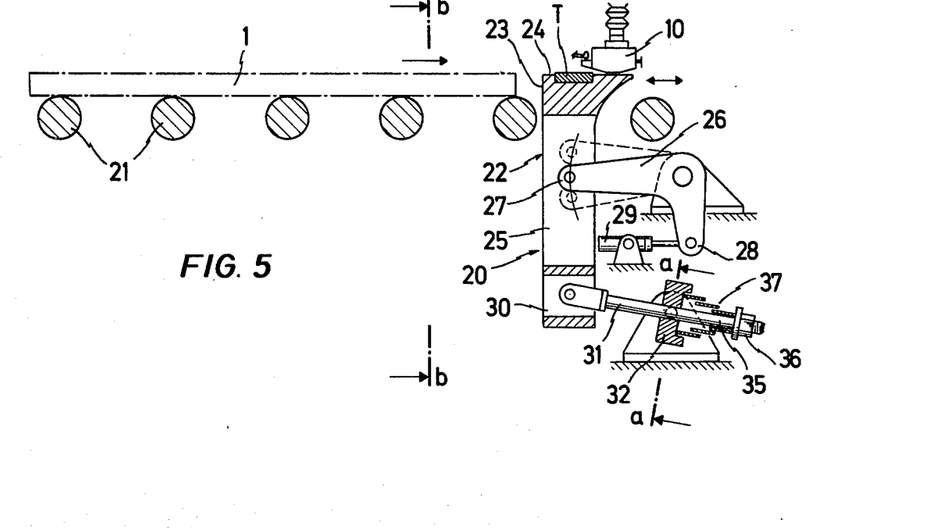
FIG. 5 is a side elevation, partly in section, of a third embodiment of a test plate holder, the test plates being individually fitted into a holder arranged to be raisable and lowerable between two transporting rollers.
Figure 6:
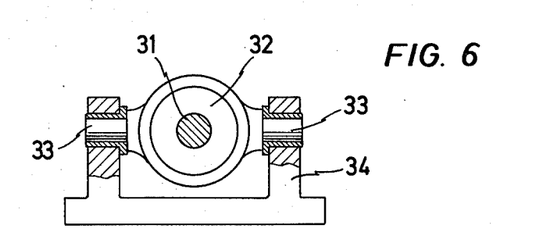
FIG. 6 is a partial section on the line a—a of FIG. 5.
Figure 7:
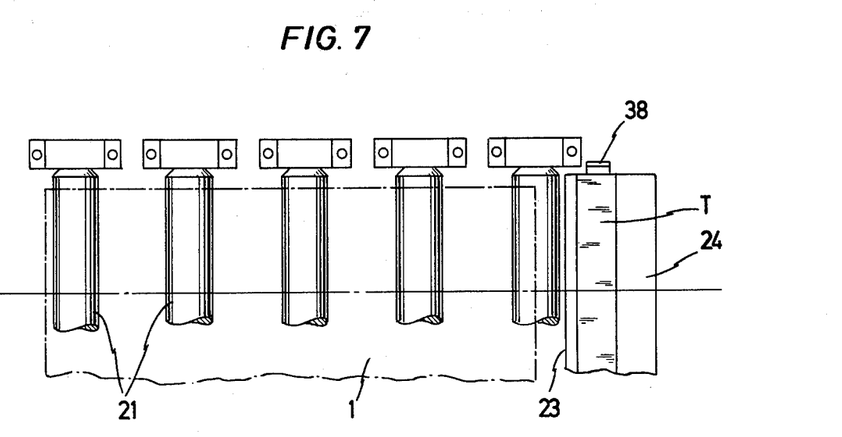
FIG. 7 is a plan view of the test plate holder shown in FIG. 5.
Figure 8:
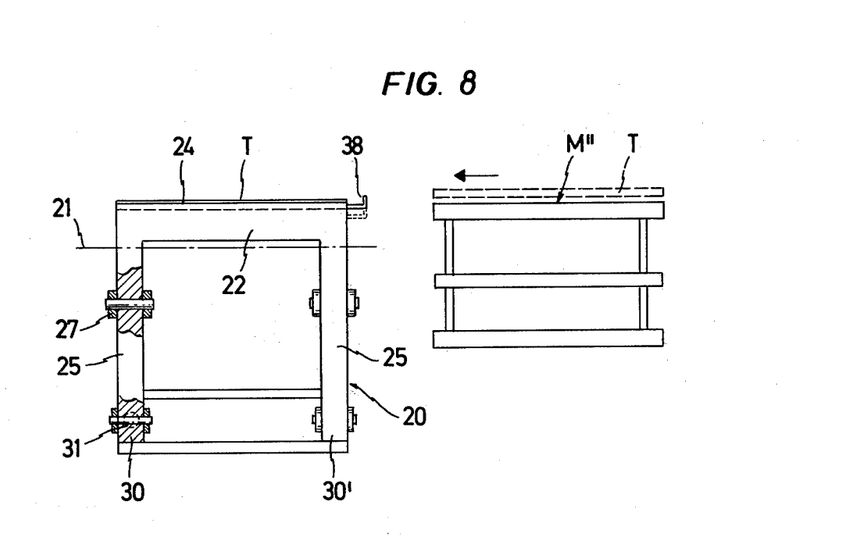
FIG. 8 is a partial elevation, partly in section, of the frame of the test plate holder shown in FIG. 5 viewed approximately from line b—b, the transporting rollers and the mechanism for moving the frame being omitted.

In the third embodiment of a test plate lifting and lowering assembly illustrated in FIGS. 5 to 8, the test plate holder 20 and the actual test plate magazine M' are adjacently arranged separately from one another. As shown in FIGS. 5 and 8 in particular, only the test plate holder 20 is designed to be raised and lowered between the transporting rollers 21 for the blanks 1 to be tested. In this case, the test plate holder 20 consists of a vertical or substantially vertical frame 22 into the upper end 24 of which the test plate T required for a certain type of blank is designed to be introduced. To enable this frame 22 to be raised and lowered, one end 27 of two angle levers 26 which are mounted for rotation at their centre is pivotally connected to the lateral frame members 25 at or substantially at the centre thereof. At their other ends 28, the angle levers 26 are each connected to a hydraulic cylinder unit 29 by means of which the test plate frame 22 is raised and lowered.

Since in this case, too, the lateral upper edge 23 of the test plate frame 22 forms the stop for the particular blank to be tested, the frame is resiliently mounted in the direction of movement of the blanks 1. To this end, a pull rod 31 is pivotally connected to the underneath 30 of each lateral frame member 25 and, substantially at its centre, is guided for axial displacement in a bearing 32. This bearing 32 is pivotally mounted by means of two pivots 33 arranged at a right angle to the pull rod axis in a pedestal 34 (cf. FIG. 6). A telescopic helical leaf spring 37 is arranged between an adjusting nut 36 screwed onto the free end 35 of the pull rod 31 and the pull rod bearing 32, absorbing the impact of the blank 1 travelling onto the upper lateral edge 23 of the frame in conjunction with the same helical leaf spring arranged on the other lower lateral frame member 30'.

In order to enable the test plate T to be introduced into and fixed in the actual test plate holder at the upper end 24 of the upper frame member from the test plate magazine M'' arranged adjacent the test plate lifting and lowering unit 20, a stop 38 is provided on one of the narrow ends of the upper frame member, being designed to be lowered and raised again after the test plate T has been introduced.

As shown in FIGS. 9 and 10 in particular, the test plate T is in the form of a rectangular slat substantially corresponding to the length or width of the blanks to be inspected and comprises narrow notches or slots simulating defects. In the surface of the test plate T, there are several rows 40 of narrow notches or slots 41a to 41d arranged at right-angles to the length thereof at the same intervals from one another as the sensors or inspecting heads 10, the notches or slots extending at an acute angle, at a right angle and parallel to the direction of the rows. In the embodiment illustrated, four groups 42a to 42d of three slots 41a to 41d oriented in different directions, but having the same orientation in each group 40, are formed in each row 40 in the test plate T in such a way that the three slots 41a to 41d of each group have different depths which are arranged in the same way in all four groups 42a to 42d. Preferably the test apparatus is constructed according to GB-PS 1 517 775 and the detected defects are classified, according to their depth, into a plurality of classes. In this case it is advantageous to associate two slots to each limiting value of depth limiting two depth classes against each other, one of the slots having a depth reduced by a predetermined percentage with respect to this limiting value of depth and the depth of the other slot being increased by about the same percentage with respect to this limiting value of depth, advantageously said percentage being about equal to the measurement accuracy of the test apparatus, preferably however somewhat larger. The correct classification of the defects simulated by slots having depths as described above into the depth classes of the test apparatus can be checked automatically when the sequence of the depth classes indicated by the test apparatus when traveling over the test plate is programmed in a computer and discrepancies of this sequence are indicated by said computer.

Preferably the slots are spaced from one another along the rows 40 of the test plate which spacings are dimensioned in such a manner that the slots do not overlap each other in the direction of the rows 40. The extension of the individual slots are preferably at least equal to the diameter of the test coils of the test apparatus or inspecting heads 10, e.g. 40 or 60 mm.

For the exact adjustment of the height of the test plate to the level of the surface to be inspected of each individual steel slab 1 preferrably photocell means are used which permit automatic working and may for example be installed in the embodiment shown in FIG. 1 in the area of the abutment surface 13 of the pedestal 9 directly beneath the surface 12, a light beam may be directed toward the photocell means by means of a source of light which is arranged at the other side of the steel slab 1 opposite the stop 13 at the same level as the photocell means raisable and lowerable with the pedestal 9. Feeler means or probe means may also be used instead of the photocells.

What is claimed is:

1. A method for testing the serviceability and for setting and calibrating a test apparatus for the non-destructive electrical, magnetic and/or magneto-inductive testing of steel slabs of different thickness and with different electrical and/or magnetic parameters for defects such as surface or below-surface cracks, laps, shrinkholes, blowholes or the like, comprising at least one inspecting head or sensor capable of detecting defects such as these and mounted for displacement relative to the surface of the slab to be tested, the slabs being delivered to the area of the test apparatus by means of transporting means, such as transporting rollers arranged at intervals from one another, characterized in that one or more test plates simulating a defective slab and having the same electrical and/or magnetic parameters as the slab are arranged in a raisable and lowerable test plate holder along one side of the slab to be tested, said test plate or plates extending substantially along the whole length of said side of said slab, and by raising or lowering said test plate holder are brought into a position in which they are in substantial alignment with the upper surface of the slab to be tested, and for setting said test apparatus said sensor is brought into contact with the surface of the test plate or plates and/or the surface of the test plate holder, which surface of the test plate holder is in alignment with the surface of the test plate or plates, and the sensor, when travelling towards and/or away from the upper surface of the slab to be tested simultaneously travels over the test plate or plates, and, while doing so, is tested for working order and calibrated.

2. A method as claimed in claim 1, characterized in that at least one of the test plates is arranged in such a way adjacent the path of travel along which the slabs move on the transporting means that the sensors or inspecting heads of the test apparatus move over the test plate during movement thereof with respect to the surface of the slab to be tested for detecting defects.

3. A method as claimed in claim 1, characterized in that the test plate or plates are introduced to the path of travel of the slabs on the transporting means, preferably between two transporting rollers, so that they are in substantial alignment with the surface of the slab to be tested, and are, after they have been traveled over by said sensors or inspecting heads, moved away from the path of travel of the slabs.

4. A method as in claim 3, wherein said movement of the test plate or plates away from the path of travel of the blanks comprise movement in at least a downward direction.

5. A method according to claim 3 or 4, wherein said movement of the test plate or plates away from the path of travel of the blanks comprises movement in a sideward direction.

6. A method according to claim 2, wherein said sensors or inspecting heads move over said one of the test plates directly before their travel along the surfaces of the slab to be tested.

7. A method according to claim 2, wherein said sensors or inspecting heads move over said one of the test plates directly after their travel along the surfaces of the slab to be tested.

8. An arrangement for testing the serviceability and for setting and calibrating a test apparatus for the non-destructive electrical, magnetic and/or magnetoinductive testing of steel slabs of different thickness and with different electrical and/or magnetic parameters for defects such as surface or below-surface cracks, laps, shrinkholes, blowholes or the like, comprising at least one sensor or inspecting head capable of detecting defects such as these and mounted for displacement relative to the surface of the slab to be tested, the slabs being delivered to the area of the test apparatus by means of a transporting system, such as transporting rollers arranged at intervals from one another, characterized in that laterally adjacent the transporting system an assembly of a test plate holder for a particular test plate corresponding to the slab to be tested and magazine (M) containing several test plates (T) that are constructed to simulate a defective slab and have the same electrical and/or magnetic parameters as the slab to be tested is arranged in the area of travel of the testing apparatus (10) at least one of said test plate holder and said magazine being raisable and lowerable along one side of the slab to be tested, at least one of said test plates being held by said test plate holder at an upper test position so as to extend substantially along the whole length of said side of said slab and, by raising and lowering of said one of said test plate holder and said magazine, being alignable with the upper surface of the slab to be tested, and in that, for setting of said test apparatus, said sensor or detecting head is operable to be brought into contact with at least one of a surface of said test plate and a surface of said magazine that is in alignment with said surface of the test plate in such a manner that said sensor or detecting head travels over the test plate during at least one of its movements toward and away from the upper surface of the slab to be tested for testing and calibrating of said sensor or detecting head.

9. An arrangement according to claim 8, characterized in that the test plate is in the form of a rectangular slat and, over its length corresponding to a dimension of the blanks (1) to be inspected, comprises several rows (40) of narrow notches or slots that are configured for simulating defects (41a to d) and which are arranged so as to correspond in spacing from one another, in a direction of movement of a test apparatus, to the same interval as the sensors or inspecting heads of said test apparatus (10), at least some of said notches or slots extending at an acute angle, at a right angle and parallel to the direction of movement of the test apparatus (10) and differing from one another in depth (FIGS. 9 and 10).

10. A test plate as claimed in claim 9 characterized in that each of said several rows (40) contains four groups (42a to d) of notches (41a to d) differing in their orientation, the notches arranged with the same orientation in each group (42a to d) having different depths which are arranged in the same order in all groups (42a to d).

11. An arrangement as claimed in claim 8, characterized in that the test plates (T) contained in the magazine (M) are arranged on a chain conveyor (2) one behind the other in the travel direction, this chain conveyor being operable to bring a test plate (T) adapted to the parameters of the slab to be inspected into said upper test position.

12. An arrangement as claimed in claim 8, characterized in that a magazine (M') containing several test plates is fixedly mounted in the area of the testing apparatus (10) beside the transporting system (21) for the slabs (1) and respectively only one test plate (T) is raisable to and lowerable from the level of the surface of the slab to be inspected (FIGS. 3 and 4).

13. An arrangement as claimed in claim 8, characterized in that the test plates (T) contained in the magazine (M') are arranged one behind the other on a chain conveyor (2) in its direction of travel and only that test plate (T) which is adapted to the slab (1) to be inspected is individually raisable and lowerable by means of said test plate holder (8, 9, 14) in conjunction with hydraulic cylinder units (15).

14. An arrangement according to claim 8, wherein said test plate holder and magazine are formed as a single unit.

15. An arrangement according to claim 8, wherein said test holder is formed as a separate unit from said magazine.

16. An arrangement as claimed in claim 15, characterized in that said test holder (20) for the particular test plate (T) adapted to the parameters of the slab (1) to be inspected is arranged in the area of the testing apparatus (10) between two adjacent transporting rollers (21) of the system for transporting the slabs in such a way that it can be raised and lowered, the test plate (T) being delivered to this holder (20) from said test plate magazine which is arranged laterally thereof (M''), (FIGS. 5 to 8).

17. An arrangement as claimed in claim 16, characterized in that the test plate holder consists of a vertically or substantially vertically arranged frame (22) into the upper end (24) of which the test plate (T) is designed to be introduced and which along its sides (25) at or substantially at the center thereof is pivotally supported by one end (27) of an angle lever (26) which is rotatably mounted at its center and, at its other end (28), is connected to a hydraulic cylinder unit (29) by means of which the frame (22) can be raised and lowered, a pull rod (31) being pivotally mounted on the underneath (30) of each of said sides (25) and being guided for axial displacement against the force of a spring (37) in a pivotal bearing (32).

18. An arrangement as claimed in claim 17, characterized in that said pivotal bearing (32) in which the pull rod (31) is axially guided is pivotable about two pivots (33) arranged opposite one another at right angles to the pull rod axis in a pedestal (34) and in that said spring is a compression spring (37) arranged between the pull rod bearing (32) and an adjusting nut (36) screwed onto the free end (35) of the pull rod (31).

19. An arrangement as claimed in claim 18, characterized in that the spring (37) is a telescopic helical leaf spring.

* * * * *